(12) United States Patent
Wei et al.

(10) Patent No.: US 10,048,246 B2
(45) Date of Patent: Aug. 14, 2018

(54) BIOLOGICAL DETECTING CARTRIDGE AND FLOWING METHOD OF DETECTED FLUID THEREOF

(71) Applicant: SKYLA CORPORATION HSINCHU SCIENCE PARK BRANCH, Hsinchu (TW)

(72) Inventors: Chia-Chun Wei, Taipei (TW); Hung-Wei Chen, Taipei (TW)

(73) Assignee: SKYLA CORPORATION HSINCHU SCIENCE PARK BRANCH, Hsinchu (TW)

( * ) Notice: Subject to any disclaimer, the term of this patent is extended or adjusted under 35 U.S.C. 154(b) by 192 days.

(21) Appl. No.: 15/196,043

(22) Filed: Jun. 29, 2016

(65) Prior Publication Data

US 2017/0307586 A1    Oct. 26, 2017

(30) Foreign Application Priority Data

Apr. 20, 2016    (CN) .......................... 2016 1 0246839

(51) Int. Cl.
*B01L 3/00*    (2006.01)
*G01N 33/487*    (2006.01)
(Continued)

(52) U.S. Cl.
CPC ...... *G01N 33/4875* (2013.01); *B01L 3/50273* (2013.01); *B01L 3/502753* (2013.01); *G01N 1/10* (2013.01); *G01N 1/38* (2013.01); *G01N 33/49* (2013.01); *B01L 2200/0621* (2013.01); *B01L 2300/087* (2013.01);
(Continued)

(58) Field of Classification Search
CPC ..... B01L 2400/0409; B01L 2300/0816; B01L 3/50273; B01L 2200/0621; B01L 2300/087
See application file for complete search history.

(56) References Cited

U.S. PATENT DOCUMENTS 4,814,282 A * 3/1989 Holen ....................... B04B 5/02
250/576
4,883,763 A * 11/1989 Holen ................. B01L 3/50273
356/246

(Continued)

FOREIGN PATENT DOCUMENTS

EP    1669733    6/2006
EP    2332653    6/2011
(Continued)

OTHER PUBLICATIONS

"Office Action of Japan Counterpart Application," dated Aug. 15, 2017, p. 1-p. 3.

(Continued)

*Primary Examiner* — David A Rogers
(74) *Attorney, Agent, or Firm* — JCIPRNET (57) ABSTRACT

A biological detecting cartridge adapted to gather a detected fluid includes a collection port, a first flowing layer structure communicating with the collection port and a second flowing layer structure communicating with the first flowing layer structure. The first and the second flowing layer structures are disposed in different levels in the biological detecting cartridge. A flowing method of a detected fluid in a biological detecting cartridge is further provided.

11 Claims, 8 Drawing Sheets

(51) Int. Cl.
 *G01N 1/10* (2006.01)
 *G01N 1/38* (2006.01)
 *G01N 33/49* (2006.01)
(52) U.S. Cl.
 CPC .............. *B01L 2300/0867* (2013.01); *B01L 2300/0874* (2013.01); *B01L 2300/0887* (2013.01); *B01L 2400/0409* (2013.01)

(56) References Cited

U.S. PATENT DOCUMENTS

| | | | | |
|---|---|---|---|---|
| 4,940,527 | A * | 7/1990 | Kazlauskas | G01N 33/491 204/401 |
| 8,475,734 | B2 * | 7/2013 | Neijzen | B01L 3/502753 422/408 |
| 8,486,336 | B2 * | 7/2013 | Kageyama | B01L 3/502738 356/246 |
| 8,883,095 | B2 * | 11/2014 | Lai | G01N 33/00 422/506 |
| 8,956,580 | B2 * | 2/2015 | Lai | B01L 3/508 422/415 |
| 9,162,227 | B2 * | 10/2015 | Borch | B01L 3/502738 |
| 9,404,912 | B2 * | 8/2016 | Fujii | G01N 33/4875 |
| 9,417,178 | B2 * | 8/2016 | Momose | B01L 3/502753 |
| 9,696,246 | B2 * | 7/2017 | Beerling | G01N 1/28 |
| 2005/0083781 | A1 | 4/2005 | Caren et al. | |
| 2006/0083667 | A1 * | 4/2006 | Kohara | B01J 19/0046 422/209 |
| 2007/0243111 | A1 * | 10/2007 | Momose | B01L 3/502738 422/400 |
| 2009/0098658 | A1 * | 4/2009 | Momose | B01L 3/5027 436/164 |
| 2009/0111675 | A1 * | 4/2009 | Yokogawa | B01L 3/50273 494/37 |
| 2009/0135407 | A1 * | 5/2009 | Kageyama | G01N 33/4915 356/39 |
| 2009/0142232 | A1 * | 6/2009 | Okada | B01L 3/502753 422/72 |
| 2009/0155125 | A1 * | 6/2009 | Michiue | B01L 3/5027 422/400 |
| 2009/0232708 | A1 * | 9/2009 | Yokogawa | B01L 3/5027 422/400 |
| 2009/0269854 | A1 * | 10/2009 | Kageyama | B01F 11/0002 436/177 |
| 2010/0281961 | A1 * | 11/2010 | Saiki | G01N 35/025 73/64.56 |
| 2013/0210129 | A1 * | 8/2013 | Selden | B01L 3/502707 435/287.2 |
| 2013/0302787 | A1 * | 11/2013 | Agarwal | C12N 15/1006 435/5 |
| 2013/0309149 | A1 * | 11/2013 | Lai | B01L 3/508 422/554 |
| 2014/0170641 | A1 * | 6/2014 | Macemon | G01N 1/00 435/5 |
| 2014/0170680 | A1 * | 6/2014 | Meissonnier | G01N 33/56972 435/7.24 |
| 2015/0284775 | A1 * | 10/2015 | Egan | C12Q 1/6844 506/9 |
| 2015/0316534 | A1 * | 11/2015 | Delmenico | G01N 33/4905 422/73 |
| 2016/0209431 | A1 * | 7/2016 | Battrell | B01L 3/502776 |
| 2016/0237482 | A1 * | 8/2016 | Bickel | B01L 3/502715 |
| 2017/0014821 | A1 * | 1/2017 | Carrera Fabra | C12Q 1/68 |
| 2017/0036210 | A1 * | 2/2017 | Corey | B01L 7/52 |

FOREIGN PATENT DOCUMENTS

| | | |
|---|---|---|
| JP | H02889704 | 3/1990 |
| JP | 2007513757 | 5/2007 |
| JP | 2007333716 | 12/2007 |
| JP | 2015105891 | 6/2015 |
| WO | 2011081530 | 7/2011 |

OTHER PUBLICATIONS

"Search Report of Europe Counterpart Application," dated Aug. 7, 2017, p. 1-p. 18.

* cited by examiner

BIOLOGICAL DETECTING CARTRIDGE AND FLOWING METHOD OF DETECTED FLUID THEREOF

CROSS-REFERENCE TO RELATED APPLICATION

This application claims the priority benefit of China application no. 201610246839.2, filed on Apr. 20, 2016. The entirety of the above-mentioned patent application is hereby incorporated by reference herein and made a part of this specification.

BACKGROUND

Field of the Invention

The invention relates to a detecting cartridge and a flowing method of a detected fluid thereof. More particularly, the invention relates to a biological detecting cartridge and a flowing method of a detected fluid thereof.

Description of Related Art

Generally, in order to reduce a size of a biological detecting cartridge, micro flowing channel structures are employed in the biological detecting cartridge for a detected fluid to flow in the micro flowing channel structures by means of capillarity. However, the micro flowing channels have to be manufactured in a manner with high precision in a manufacturing process, which leads to difficulty in manufacturing and high yield loss.

In addition, when a test is performed by the biological detecting cartridge, a specific quantity of the detected fluid (e.g., blood) has to be provided for being mixed with medicaments in the biological detecting cartridge. To be more specific, due to the quantity of the medicaments in the biological detecting cartridge being fixed, errors would occur in detection values if the quantity of the detected fluid to be reacted with the medicaments in the biological detecting cartridge is excessive or insufficient.

In addition, whether the detected fluid entering the biological detecting cartridge can be evenly mixed with the medicaments in the biological detecting cartridge would also significantly affect testing results. If the detected fluid and the medicaments are not evenly mixed in the biological detecting cartridge, no precise detection values can be provided to a user for reference. Especially, in a case with a trace of specimen, the detected fluid, due to being scarce, is not easily mixed with the medicaments evenly. Therefore, in order to avoid the aforementioned situation, generally, a long time has to be waited, so as to ensure that the trace of specimen and the medicaments are completely and evenly mixed in the biological detecting cartridge for subsequent biochemical tests.

SUMMARY

The invention provides a biological detecting cartridge. With the design of flowing channel structures in the biological detecting cartridge, driving forces corresponding to different directions related to the biological detecting cartridge can be applied to a detected fluid, so as to drive the detected fluid to flow in the flowing channel structures in the biological detecting cartridge. In this way, the requirement for manufacturing precision can be effectively reduced. Moreover, with the design of the flowing channel structures in the biological detecting cartridge, the detected fluid to be reacted with medicaments can be quantified, and the detected fluid can be quickly and evenly mixed with the medicaments, so as to provide a stable test result.

The invention provides a flowing method of a detected fluid in a biological detecting cartridge, by which driving forces corresponding to different directions related to the biological detecting cartridge can be applied to the detected fluid in a biological detecting cartridge at different time points, so as to drive the detected fluid to flow in flowing channel structures in the biological detecting cartridge and can be effectively and quickly mixed with medicaments evenly, and thereby, the time for mixing can be reduced.

According to an embodiment of the invention, a biological detecting cartridge adapted to gather a detected fluid is provided. The biological detecting cartridge includes a collection port, a first flowing layer structure communicating with the collection port and a second flowing layer structure communicating with the first flowing layer structure. The first and the second flowing layer structures are disposed in different levels in the biological detecting cartridge.

According to an embodiment of the invention, a flowing method of a detected fluid in a biological detecting cartridge is provided, which includes the following steps. A detected fluid is provided to a biological detecting cartridge. At a first time point, a first driving force corresponding to a first direction related to the biological detecting cartridge is applied to the detected fluid in the biological detecting cartridge. At a second time point, a second driving force corresponding to a second direction related to the biological detecting cartridge is applied to the detected fluid in the biological detecting cartridge. The first direction is different from the second direction.

To make the above features and advantages of the invention more comprehensible, embodiments accompanied with drawings are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 4 to FIG. 11 are schematic diagrams illustrating a flowing process of a detected fluid in the biological detecting cartridge of the invention.

DESCRIPTION OF EMBODIMENTS

Figure 1:
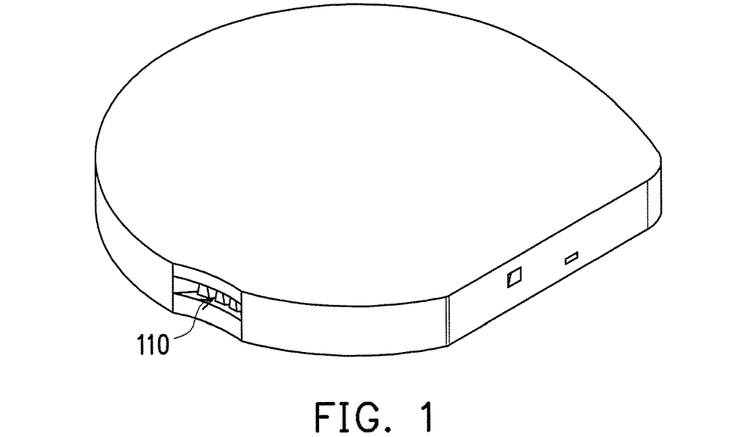
FIG. 1 is a schematic three-dimensional diagram illustrating a biological detecting cartridge according to an embodiment of the invention.
Figure 2:
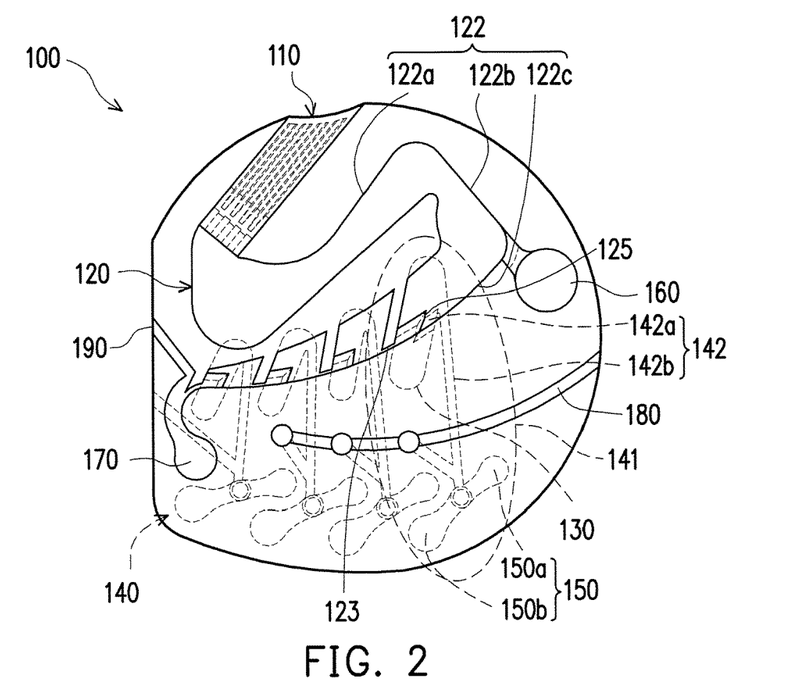
FIG. 2 is a schematic perspective top-view diagram of the biological detecting cartridge depicted in FIG. 1.

FIG. 1 is a schematic three-dimensional diagram illustrating a biological detecting cartridge 100 according to an embodiment of the invention. FIG. 2 is a schematic perspective top-view diagram of the biological detecting cartridge 100 depicted in FIG. 1. In the present embodiment, the biological detecting cartridge 100 includes a collection port 110, a first flowing layer structure 120 and a second flowing layer structure 140. The collection port 110 communicates with the first flowing layer structure 120, the first flowing layer structure 120 communicates with the second flowing layer structure 140, and the first flowing layer structure 120 and the second flowing layer structure 140 are disposed in different levels in the biological detecting cartridge 100.

In the present embodiment, the first flowing layer structure 120 and the second flowing layer structure 140 are disposed in the biological detecting cartridge 100, and the first flowing layer structure 120 is disposed above and communicates with the second flowing layer structure 140. The first flowing layer structure 120 and the second flowing layer structure 140 at least partially overlap with each other. Referring to FIG. 2, the first flowing layer structure 120 in the biological detecting cartridge 100 is represented by solid lines, while the second flowing layer structure 140 is represented by dotted lines.

In the embodiments of the invention, due to the first flowing layer structure 120 and the second flowing layer structure 140 being disposed in different levels in the biological detecting cartridge 100, and the first flowing layer structure 120 and the second flowing layer structure 140 at least partially overlapping with each other, the size of the biological detecting cartridge 100 is effectively reduced.

Referring to FIG. 1 and FIG. 2, the first flowing layer structure 120 of the biological detecting cartridge 100 of the present embodiment includes a first flowing channel 122 and a separation tank 160. The first flowing channel 122 communicates with the collection port 110 and also communicates with the separation tank 160. The second flowing layer structure 140 of the biological detecting cartridge 100 of the present embodiment includes at least one branch structure 141. The branch structure 141 includes a quantification tank 130, a second flowing channel 142 and a mixing tank set 150. The quantification tank 130 communicates with the first flowing channel 122 of the first flowing layer structure 120, and the quantification tank 130 is connected with the mixing tank set 150 through the second flowing channel 142.

In the embodiments of the invention, after a detected fluid F (illustrated in FIG. 4) enters the biological detecting cartridge 100 from the collection port 110, driving forces in corresponding directions related to the biological detecting cartridge 100 will be applied to the detected fluid F at different time points, so as to drive the detected fluid F to flow in the first flowing layer structure 120 and the second flowing layer structure 140 in the biological detecting cartridge 100.

Figure 3A:
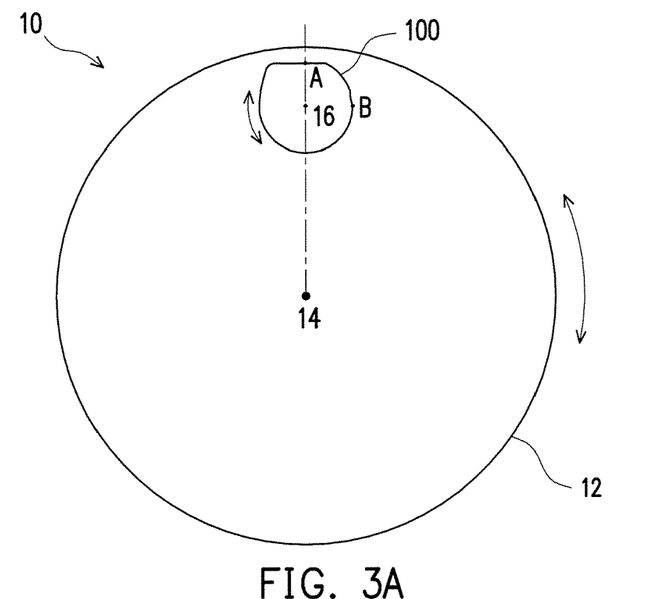
FIG. 3A and FIG. 3B are schematic diagrams illustrating a detecting device adapted for the biological detecting cartridge of the invention according to an embodiment, which respectively illustrate the relation between the biological detecting cartridge and the detecting device at different time points.
Figure 3B:
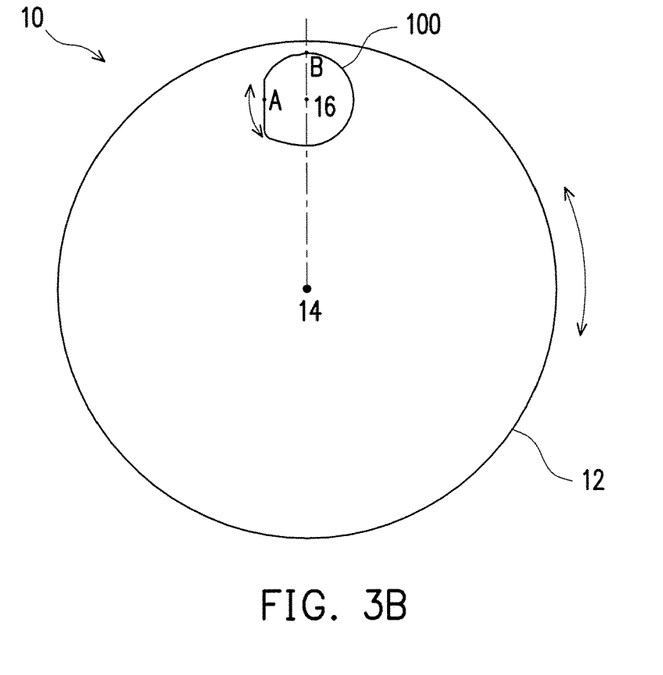

Referring to FIG. 3A and FIG. 3B, FIG. 3A and FIG. 3B are schematic diagrams illustrating a detecting device 10 adapted for the biological detecting cartridge 100 of the invention according to an embodiment, which respectively illustrate the relation between the biological detecting cartridge 100 and the detecting device 10 at different time points. In the present embodiment, the detecting device 10 includes a rotatable base 12. The rotatable base 12 rotates around a first rotation axis 14. The biological detecting cartridge 100 is placed on the rotatable base 12 and can rotate relatively to the rotatable base 12 around a second rotation axis 16. The first rotation axis 14 and the second rotation axis 16 are not coaxial. In addition, the biological detecting cartridge 100 may also revolve round the first rotation axis 14 through the rotation of the rotatable base 12. In other words, the biological detecting cartridge 100 may make revolution round the first rotation axis 14 and may also revolve on the second rotation axis 16.

In the detecting device 10 of the present embodiment, after the biological detecting cartridge 100 rotates around the second rotation axis 16 to corresponding angles at different time points, the rotatable base 12 drives the biological detecting cartridge 100 to revolve round the first rotation axis 14, such that centrifugal forces in corresponding directions related to the biological detecting cartridge 100 may be applied to the detected fluid F.

For instance, it is assumed that at a first time point, the biological detecting cartridge 100 rotates around the second rotation axis 16 to an angle and is positioned as illustrated in FIG. 3A. At the position as illustrated in FIG. 3A, point A on the biological detecting cartridge 100 is located on an extension line of a connection line between the first rotation axis 14 and the second rotation axis 16. In this circumstance, when the rotatable base 12 drives the biological detecting cartridge 100 to revolve round the first rotation axis 14, a centrifugal force in a direction toward point A will be applied to the detected fluid F in the biological detecting cartridge 100, so that the detected fluid F will flow toward point A.

Then, it is assumed that at a second time point, the biological detecting cartridge 100 rotates around the second rotation axis 16 to an angle and is positioned as illustrated in FIG. 3B. At the position as illustrated in FIG. 3B, point B on the biological detecting cartridge 100 is located on the extension line of the connection line of the first rotation axis 14 between the second rotation axis 16. In this circumstance, when the rotatable base 12 drives the biological detecting cartridge 100 to revolve round the first rotation axis 14, a centrifugal force in a direction toward point B will be applied to the detected fluid F in the biological detecting cartridge 100, so that the detected fluid F will flow toward point B.

Through the detecting device 10, the detected fluid F in the biological detecting cartridge 100 may receive the driving forces in the corresponding directions related to the biological detecting cartridge 100 at different time points, so as to flow toward different directions related to the biological detecting cartridge 100, and flow in the first flowing layer structure 120 and the second flowing layer structure 140 in the biological detecting cartridge 100. In the invention, the detecting device 10 is not limited to the embodiment described above. In the invention, the detecting device 10 is mainly adapted to apply the driving forces in the corresponding directions related to the biological detecting cartridge 100 to the detected fluid F in the biological detecting cartridge at different time points. In another embodiment, the detecting device 10 may also drive the biological detecting cartridge provided by the invention to move toward different directions at different time points, to achieve applying the driving forces in the corresponding directions related to the biological detecting cartridge 100 to the detected fluid F in the biological detecting cartridge at different time points.

In the embodiments of the invention, the detected fluid F moves in the biological detecting device 10 in a manner that the detected fluid F is moved to different positions in the biological detecting device 10 through the driving forces (e.g., the centrifugal forces) with different directions related to the biological detecting cartridge 100 applied to the detected fluid F. Thus, the precision requirements for sizes of the flowing channels in the biological detecting device 100 are less strict, which brings more convenience and advantages of good yield and low cost to the manufacturing process.

Figure 4:
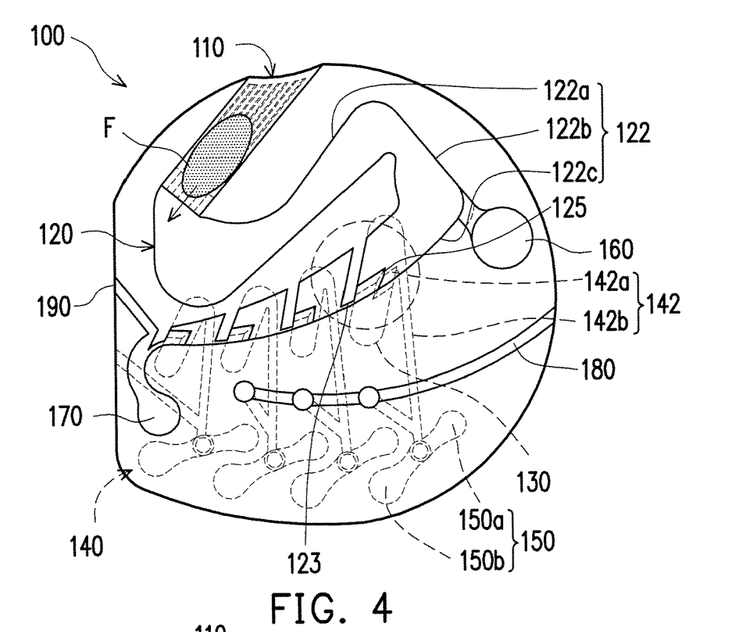
Figure 9:
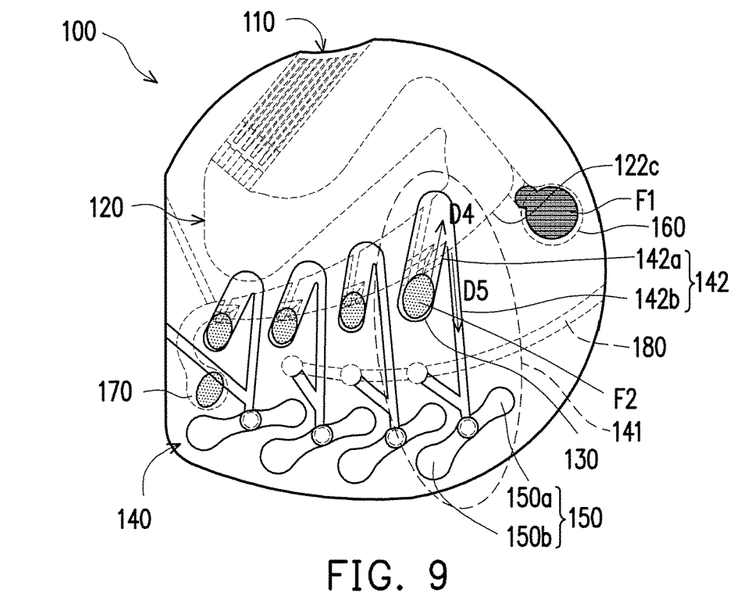
Figure 10:
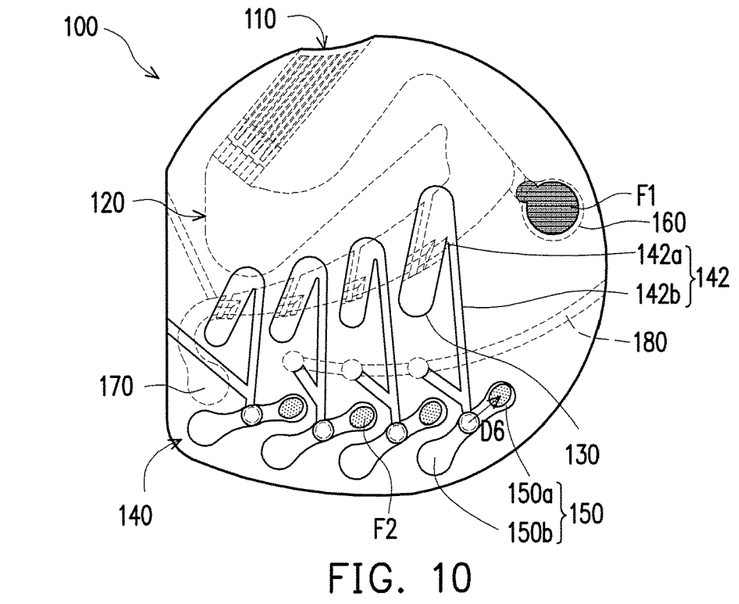
Figure 11:
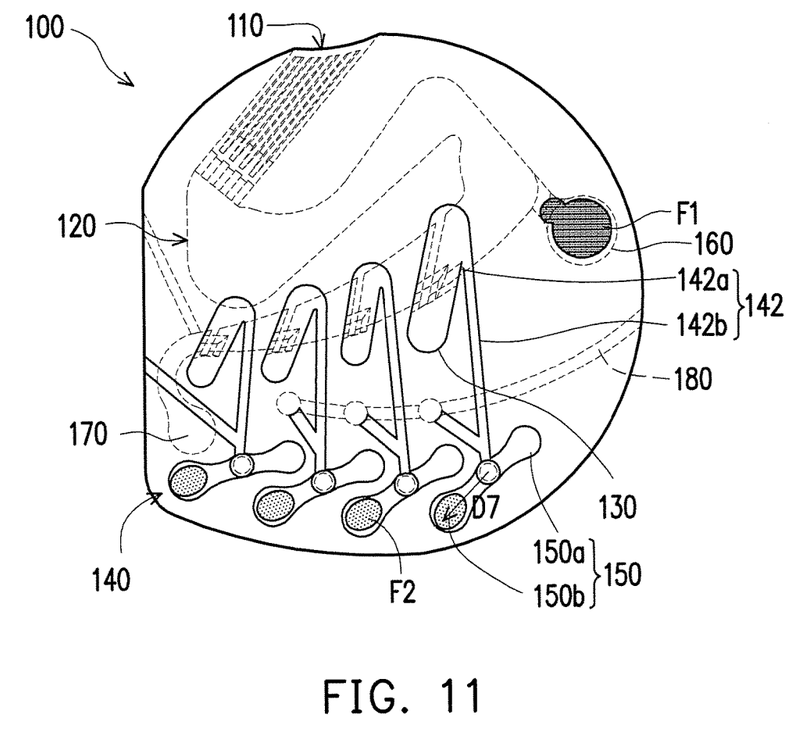

FIG. 4 and FIG. 11 are schematic diagrams illustrating a flowing process of the detected fluid F in the biological detecting cartridge 100 of the invention. In FIG. 4 to FIG. 6 and FIG. 8, the first flowing layer structure 120 in the biological detecting cartridge 100 is represented by solid lines, while the second flowing layer structure 140 is represented by dotted lines. In FIG. 9 to FIG. 11, the first flowing layer structure 120 in the biological detecting cartridge 100 is represented by dotted lines, while the second flowing layer structure 140 is represented by solid lines. The internal structure of the biological detecting cartridge 100 will be introduced in detail below, and a flowing and mixing method of the detected fluid F in the biological detecting cartridge 100 will be described as well.

Figure 5A:
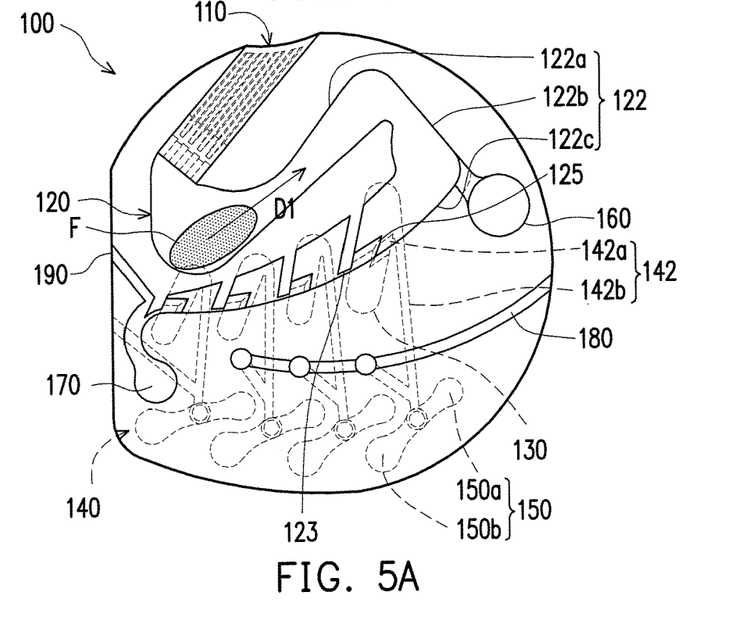

Referring to FIG. 4 and FIG. 5A, the detected fluid F enters the biological detecting cartridge 100 from the collection port 110 and then, enters the first flowing channel 122 communicating with the collection port 110. After the detected fluid F enters the first flowing channel 122, the detecting device 10 applies a driving force in a corresponding direction to the detected fluid F according to an extension direction of the first flowing channel 122, so as to drive the detected fluid F to flow along the first flowing channel 122.

In the present embodiment, the first flowing channel 122 includes a plurality of first sections 122a, 122b and 122c, wherein the first sections are sequentially connected and the two adjacent first sections are connected with an angle. To be more specific in the embodiment, the first flowing channel 122 includes three first sections 122a, 122b and 122c connected in series, and the connections between two adjacent sections of the first sections 122a, 122b and 122c have a bend. Accordingly, the extension directions of the corresponding first sections 122a, 122b and 122c are not all the same. In order to drive the detected fluid F to sequentially flow through the first sections 122a, 122b and 122c along the first flowing channel 122, the detecting device 10 applies driving forces respectively in parallel to extension directions of the first sections 122a, 122b and 122c to the detected fluid F at different time points based on the extensions directions of the first sections 122a, 122b and 122c.

Figure 5B:
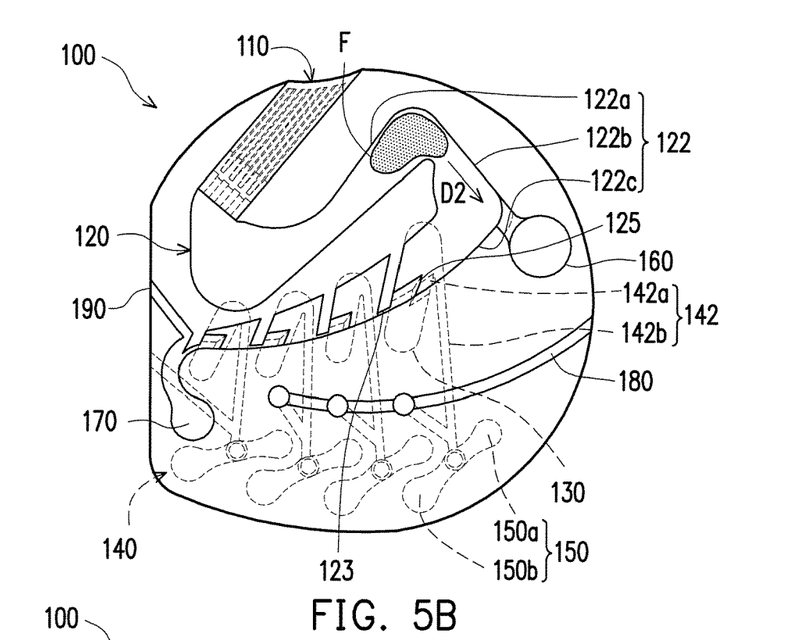
Figure 6:
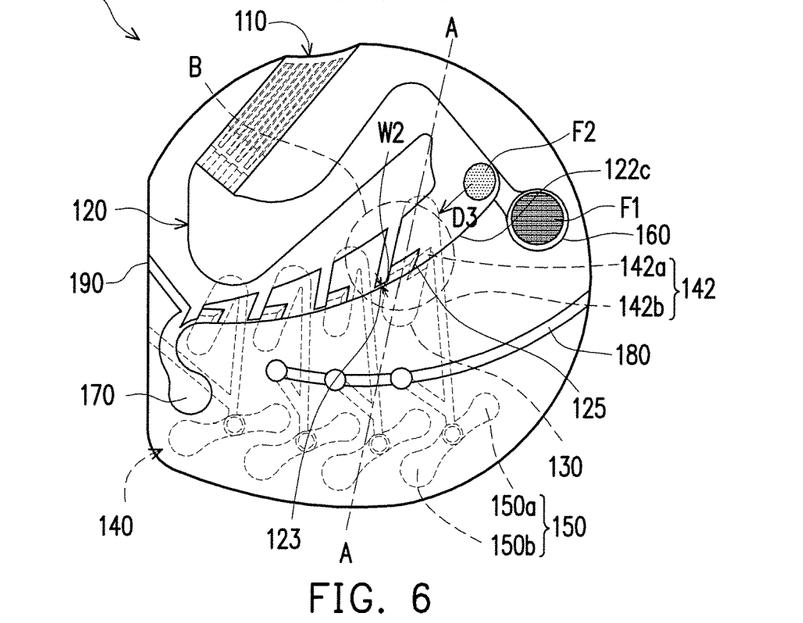

For example, referring to FIG. 5A, in order to drive the detected fluid F to flow through the first section 122a, the detecting device 10 applies a driving force D1 in parallel to the extension direction of the first section 122a to the detected fluid F according to the extension direction of the first section 122a, such that the detected fluid F flows through the first section 122a and is gathered at the bend between the two first sections 122a and 122b, as illustrated in FIG. 5B. Then, in order to drive the detected fluid F to flow through the next first section 122b, the detecting device 10 applies a driving force D2 in parallel to the extension direction of the first section 122b to the detected fluid F according to the extension direction of the first section 122b, such that the detected fluid F flows through the first section 122b and is gathered at the bend between the two first sections 122b and 122c, as illustrated in FIG. 6. The rest may be deduced by analogy.

In the present embodiment, the first flowing channel 122 includes the three first sections 122a, 122b and 122c connected in series, and a bend is designed at the connections between two adjacent sections of the first sections 122a, 122b and 122c, which contributes to preventing the detected fluid F from flowing back during the process of applying the driving forces corresponding to different directions to the detected fluid F to drive the detected fluid F to flow in the first flowing channel 122. However, the number of the first sections is not limited thereto, and a person skilled in the art may design the first sections in different numbers based on actual demands. The flowing method of the detected fluid F in each first section is similar to that described above and thus, will not be repeatedly described.

Referring to FIG. 6, the separation tank 160 of the first flowing layer structure 120 is connected with the bend between two of the first sections, e.g., 122b and 122c, and an extension direction of the separation tank 160 is parallel to one of the first sections, e.g., 122b. Herein, the detected fluid F sequentially flows through the first sections 122b and 122c, and the extension direction of the separation tank 160 is parallel to one of the two first sections 122b and 122c, i.e., the first section 122b, which the detected fluid F first flows through. Referring to FIG. 5B, the separation tank 160 is connected with the bend between the two first sections 122b and 122c, and since the detected fluid F flows through the first section 122b first and then the first section 122c, the extension direction of the separation tank 160 is parallel to the first section 122b.

In the present embodiment, the separation tank 160 of the first flowing layer structure 120 is adapted to separate component parts having different densities contained in the detected fluid F through continuously applying the driving force toward the extension direction of the separation tank 160 to the detected fluid F. As the driving force is continuously applied, a first component part F1 of the detected fluid F having a greater density flows into the separation tank 160, while a second component part F2 of the detected fluid F having a smaller density remains in the first flowing channel 122, as illustrated in FIG. 6.

In an example that the detected fluid F is blood F, the blood F contains a first component part F1 having the greater density (i.e., corpuscles F1) and a second component part F2 having the smaller density (i.e., blood plasma F2) which are mixed. The blood F flows in the biological detecting cartridge 100 through a driving force (e.g., a centrifugal force). Referring to FIG. 5B, after the driving force D2 in parallel to the extension direction of the first section 122b is applied to the blood F to drive the blood F to flow through the first section 122b and gather at the bend between the two first sections 122b and 122c, the detecting device 10 continues to apply the driving force D2 toward the extension direction of the separation tank 160 to the blood F, such that the corpuscles F1 having the greater density move to the separation tank 160, while the blood plasma F2 having the smaller density stays in the first flowing channel 122, as illustrated in FIG. 6. Certainly, in other embodiments, if the biological detecting cartridge 100 does not have to separate the detected fluid into the component parts having different densities, the design of the separation tank 160 may be omitted.

In the present embodiment, the first flowing layer structure 120 is connected with and communicates with the at least one branch structure 141 of the second flowing layer structure 140 through one of the first secions 122a, 122b and 122c (which refers to 122c in this case) of the first flowing channel 122, and the first section 122c connected with the branch structure 141 is also referred to as a connection section 122c. In other words, the plurality of first sections 122a, 122b and 122c of the first flowing channel 122 include the connection section 122c connected with the branch structure 141. In the present embodiment, the connection section 122c has a corresponding structure designed in collocation with the branch structure 141, which will be subsequently described together with the second flowing layer structure 140.

Referring to FIG. 2, the second flowing layer structure 140 includes at least one branch structure 141. The branch structure 141 includes a quantification tank 130, a second flowing channel 142 and a mixing tank set 150. The quantification tank 130 communicates with the connection section 122c of the first flowing channel 122, the second flowing channel 142 communicates with the quantification tank 130, and the mixing tank set 150 communicates with the second flowing channel 142. In the present embodiment, the second flowing layer structure 140 is disposed under the first flowing layer structure 120, and the quantification tank 130 partially overlaps and communicates with the connection section 122c of the first flowing channel 122.

Continuously referring to FIG. 6, after the blood F flowing through the separation tank 160 is separated into the component parts having different densities, the blood plasma F2 having the smaller density is located in the first flowing channel 122 and is gathered at the bend between the first sections 122b and 122c. Then, a driving force D3 in parallel to the extension direction of the first section 122c is applied to the blood plasma F2. During the process of the blood plasma F2 being driven by the driving force D3 to flow in the connection section 122c, the blood plasma F2 preferentially enters the quantification tank 130 of the second flowing layer structure 140 through the structure disposed in the connection section 122c designed correspondingly to the branch structure 141, which will be described in detail below.

In another embodiment of the invention, if the biological detecting cartridge 100 does not have to separate the detected fluid into the component parts having different densities, and the design of the separation tank 160 is omitted, after the detected fluid F flows through the first section 122b and is gathered at the bend between the first sections 122b and 122c, the driving force D3 in parallel to the extension direction of the connection section 122c may also be continuously applied to the detected fluid F in the same way, and the detected fluid F may preferentially enter the quantification tank 130 of the second flowing layer structure 140 through the structure disposed in the connection section 122c corresponding to the branch structure 141.

Figure 7:
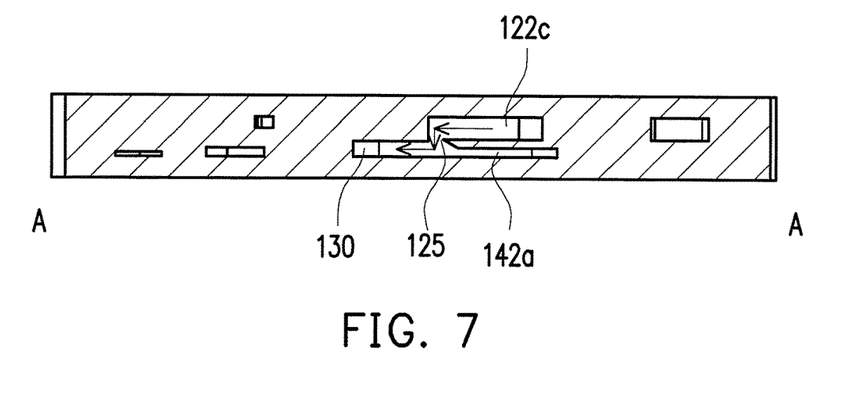
Figure 8:
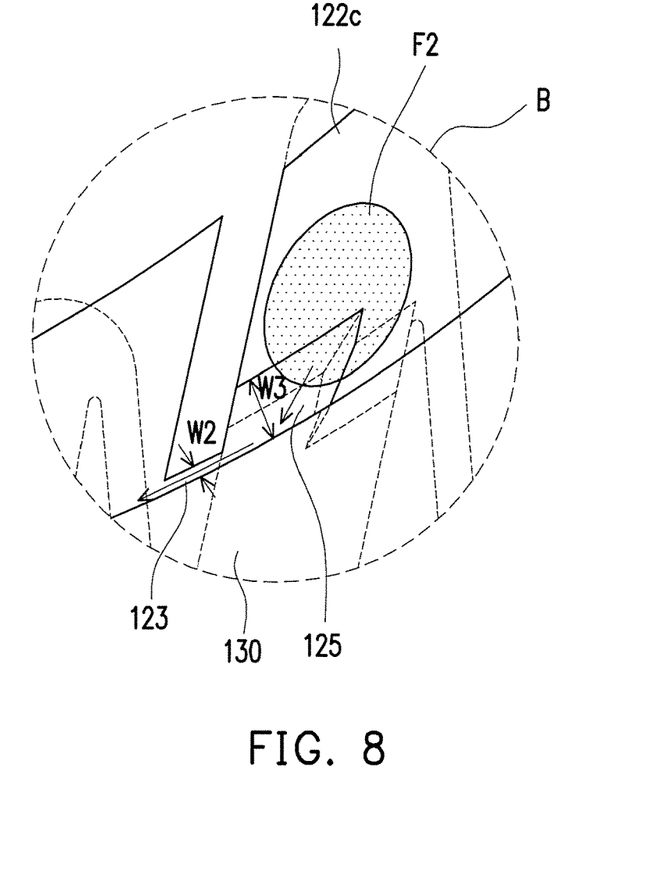

Referring to FIG. 2 and FIG. 6 to FIG. 8, FIG. 7 is a schematic cross-sectional diagram along line A-A of FIG. 6, and FIG. 8 is a schematic partially enlarged diagram of FIG. 6. The connection section 122c has a narrowed channel 123 and a communication hole 125 corresponding to the branch structure 141. The connection section 122c communicates with the quantification tank 130 of the branch structure 141 through the communication hole 125. A flow section width W3 of the communication hole 125 is greater than a flow section width W2 of the narrowed channel 123, and the communication hole 125 is located at a side of the narrowed channel 123 where the detected fluid enters. In other words, the detected fluid F flows through the communication hole 125 first and then the narrowed channel 123.

In the present embodiment, since the flow section width W3 of the communication hole 125 is greater than the flow section width W2 of the narrowed channel 123, the detected fluid F as being driven by the driving force D3 in parallel to the extension direction of the connection section 122c first flows through the communication hole 125 and into the quantification tank 130. After the quantification tank 130 is filled, the detected fluid F is no longer capable of flowing into the quantification tank 130 through the communication hole 125, and thus, the overflowing detected fluid F is driven by the driving force D3, enters the narrowed channel 123 and flows through the narrowed channel 123.

Referring to FIG. 6 first, in the example that the detected fluid F is the blood F, after the blood F flowing through the separation tank 160 is separated into the component parts having different densities, the driving force D3 in parallel to the extension direction of the connection section 122c is applied to the blood plasma F2 gathered at the bend between the first section 122b and the connection section 122c. Then, referring to FIG. 7 and FIG. 8, when the blood plasma F2 flows along the connection section 122c and arrives at a position corresponding to the branch structure 141 (as illustrated in FIG. 8), the blood plasma F2 flows through the communication hole 125 and into the quantification tank 130 since the flow section width W3 of the communication hole 125 is greater than the flow section width W2 of the narrowed channel 123 (as illustrated in FIG. 7). After the corresponding quantification tank 130 is filled, the overflowing blood plasma F2 flows through the narrowed channel 123 and continues to flow along the connection section 122c. If the biological detecting cartridge 100 has multiple branch structures 141, the rest of the blood plasma F2 continues to flow along the connection section 122c and arrives at a position corresponding to the next branch structure 141, and the aforementioned flowing steps are repeated.

In the present embodiment, with the design that the narrowed channel 123 and the communication hole 125 of the connection section 122c corresponding to the quantification tank 130 have different section widths, the detected fluid F first flows in and fills the quantification tank 130, such that the detected fluid F entering the branch structure 141 has a set quantity. In the present embodiment, the biological detecting cartridge 100 has four branch structures 141. Likewise, the connection section 122c has four narrowed channels 123 and four communication holes 125, which are respectively corresponding to the quantification tanks 130 of the four branch structures 141.

According to FIG. 6 to FIG. 9, with the design that the narrowed channels 123 and the communication holes 125 of the connection section 122c corresponding to the quantification tanks 130 have different section widths, the flowing sequence of the blood plasma F2 tends to first flowing toward the quantification tanks 130 through the communication holes 125 and then flowing leftward through the narrowed channels 123. In other words, the blood plasma F2 fills the quantification tanks 130 one by one from right to left. The quantification tanks 130 may contribute to ensuring that quantity of the blood plasma flowing in the mixing tank set 150 falls within a set range, such that detection errors caused by the quantity of the blood plasma being excessive or insufficient may be prevented.

In addition, referring back to FIG. 2, in the present embodiment, the biological detecting cartridge 100 further includes a overflow tank 170 connected with one end of the first flowing channel 122 which is far away from the collection port 110. Referring to FIG. 9, after the blood plasma F2 fills the quantification tanks 130, the rest of the blood plasma F2 flows into the overflow tank 170 from the connection section 122c. Additionally, referring to FIG. 2 again, the end of the first flowing channel 122 which is far away from the collection port 110 may also communicate with an exhaust vent 190 of the biological detecting cartridge 100 for the detected fluid F to flow smoothly in the first flowing channel 122.

Referring to FIG. 9 again, in the present embodiment, the number of the branch structures 141 is illustrated as four for example; however, the number of the branch structures 141 may vary with the number of items to be tested by the biological detecting cartridge. The second flowing channel 142 of the branch structure 141 includes a plurality of second sections 142a and 142b, wherein the second sections 142a and 142b are connected with an angle. In the present embodiment, there is a bend between the two second sections 142a and 142b to prevent the blood plasma F2 from flowing back. After the blood plasma F2 flows into and is collected in the quantification tank 130, the detecting device 10 may apply a driving force D4 in parallel to an extension direction of the second section 142a to the blood plasma F2 to drive the blood plasma F2 to flow through the second section 142a and then apply a driving force D5 in parallel to an extension direction of the second section 142b to drive the blood plasma F2 to flow through the second section 142b. Likewise, in the invention, the number of the second sections 142a and 142b is not limited, and a person skilled in the art may design the second sections 142a and 142b in different numbers based on actual demands.

In the present embodiment, the mixing tank set 150 includes a first mixing tank 150a and a second mixing tank 150b which communicate with each other. The second section 142b of the second flowing channel 142 is connected with the mixing tank set 150. Referring to FIG. 10, when the blood plasma F2 flows to the connection between the second section 142b and the mixing tank set 150, a driving force D6 toward an extension direction of the first mixing tank 150a may be applied to the blood plasma F2 to drive the blood plasma F2 to flow into the first mixing tank 150a. Then, referring to FIG. 11, a driving force D7 toward an extension direction of the second mixing tank 150b is applied to the blood plasma F2 to drive the blood plasma F2 to flow into the second mixing tank 150b.

In the present embodiment, at least one of the first mixing tank 150a and the second mixing tank 150b is provided with medicaments. Alternatively, the first mixing tank 150a and the second mixing tank 150b may also be provided with different medicaments. The medicaments may be provided in the first mixing tank 150a and/or the second mixing tank 150b in advance, and after the blood plasma F2 flows into the first mixing tank 150a and/or the second mixing tank 150b, the medicaments are dissolved in the blood plasma F2.

In the present embodiment, by means of alternately applying the driving forces D6 and D7, the blood plasma F2 may flow back and forth between the first mixing tank 150a and the second mixing tank 150b to be quickly and evenly mixed with the medicaments provided in the first mixing tank 150a and/or the second mixing tank 150b, such that the time required for mixing may be reduced.

In addition, referring to FIG. 11, in the present embodiment, the biological detecting cartridge 100 further includes an exhaust channel 180. The exhaust channel 180 communicates with the second flowing channel 142 to exhaust air out of the flowing structures of the biological detecting cartridge 100, such that the detected fluid F may be prevented from being blocked by the air and stopping in the flowing structures.

Figure 12:
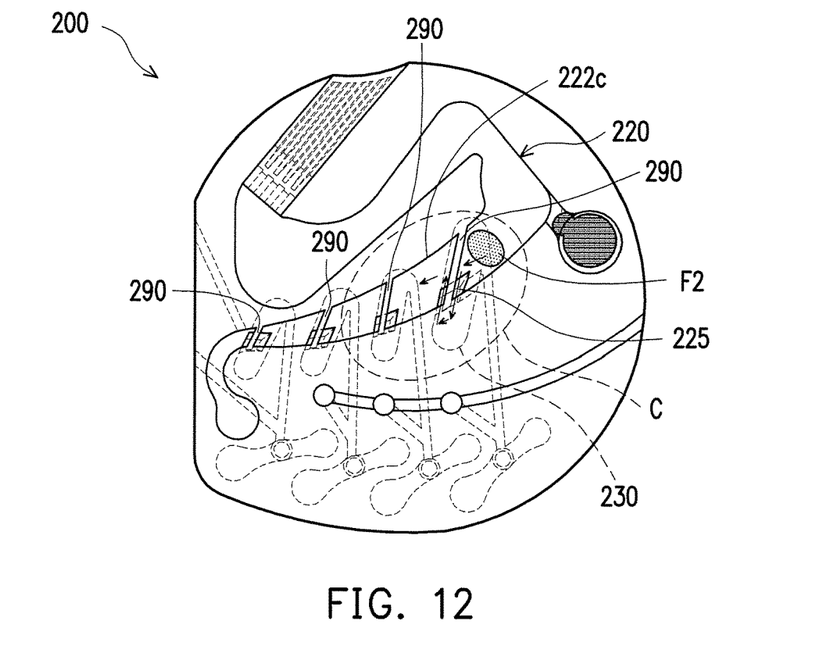
FIG. 12 is a schematic perspective diagram illustrating a biological detecting cartridge according to another embodiment of the invention.
Figure 13:
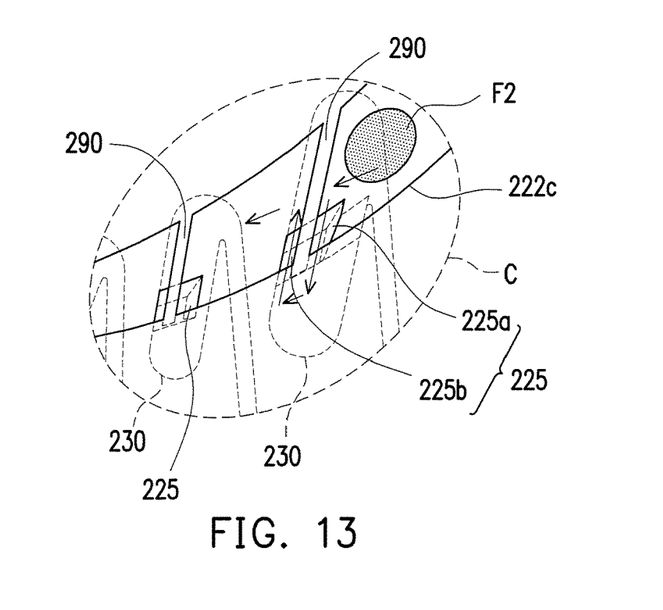
FIG. 13 is a schematic partially enlarged diagram illustrating the biological detecting cartridge depicted in FIG. 12.

FIG. 12 is a schematic perspective diagram illustrating a biological detecting cartridge 200 according to another embodiment of the invention. FIG. 13 is a schematic partially enlarged diagram illustrating the biological detecting cartridge 200 depicted in FIG. 12. Referring to FIG. 12 and FIG. 13, the main difference between the biological detecting cartridge 200 of the present embodiment and the biological detecting cartridge 100 of the preceding embodiment lies in that in the biological detecting cartridge 100 of the preceding embodiment, the narrowed channels 123 and the communication holes 125 of the connection section 122c are provided to correspond to the quantification tanks 130, while in the biological detecting cartridge 200 of the present embodiment, separators 290 and communication holes 225 of the connection section 222c are provided to correspond to quantification tanks 230.

In the preceding embodiment, the biological detecting cartridge 100 drives the detected fluid F to first flow into and fill the quantification tanks 130 through the design that the narrowed channels 123 and the communication holes 125 of the connection section 122c have different section widths. However, before the quantification tanks 130 are filled, a few quantity of the detected fluid F may still flow through the narrowed channel 123. Referring to FIG. 8, during the process of the blood plasma F2 flowing in the connection section 122c, most of the blood plasma F2 tends to passing through the communication holes 125 with the greater section width W3 and flowing toward the quantification tanks 130 in the lower layer; however, a few quantity of the blood plasma F2 may still flow along the connection section 122c toward the narrowed channels 123 with the smaller section width W2.

Referring to FIG. 12 and FIG. 13, in the present embodiment, a connection section 222c of a first flowing channel 222 of the biological detecting cartridge 200 has a separator 290 and a communication hole 225 corresponding to the quantification tanks 230. The connection section 222c communicates with the corresponding quantification tank 230 through the communication hole 225. The separator 290 is located on the communication hole 225 and divides the communication hole 225 into an inlet 225a and an outlet 225b. The inlet 225a and the outlet 225b of the communication hole 225 are respectively located at two sides of the separator 290.

In the biological detecting cartridge 200 of the present embodiment, when the blood plasma F2 flows along the connection section 222c to a position corresponding to the quantification tank 230, the blood plasma F2 is blocked by the separator 290 and flows into the quantification tank 230 first through the inlet 225a of the communication hole 225. After the corresponding quantification tank 230 is filled, the blood plasma F2 flows out from the outlet 225b of the communication hole 225 and continues to flow along the connection section 222c. If the biological detecting cartridge 200 has multiple quantification tanks 230, the rest of the blood plasma F2 continues to flow along the connection section 222c to a position corresponding to the next quantification tank 230, and the aforementioned flowing steps are repeated.

Based on the above, in the biological detecting cartridge of the invention, the first and the second flowing layer structures are disposed in different levels in the biological detecting cartridge, and thereby, the size of the biological detecting cartridge can be effectively reduced. Furthermore, with the design of the flowing channels, the separation tanks, the quantification tanks and the mixing tanks in various extension directions, the biological detecting cartridge of the invention can apply the driving forces corresponding to different directions related to the biological detecting cartridge at different time ponits, such that the detected fluid is driven to sequentially flow to corresponding positions in the biological detecting cartridge. In comparison with the conventional biological detecting cartridge in which the detected fluid flows therein by means of capillarity, the precision for the sizes of the flowing channels in the biological detecting cartridge are not highly required in the invention, which can improve the manufacturing convenience. In addition, with the structures of the connection section designed correspondingly to the quantification tanks, the quantity of the detected fluid flowing into the mixing tanks for being reacted with the medicaments in the mixing tanks can be ensured to fall within the set range, such that errors occurring in the detection values due to the quantity of the detected fluid being excessive or insufficient can be prevented. In addition, with the design of multiple mixing tanks and the driving forces corresponding to specific directions, the detected fluid can be quickly and evenly mixed with the medicaments provided in the mixing tanks, such that the time required for mixing can be reduced.

Although the invention has been disclosed by the above embodiments, they are not intended to limit the invention. It will be apparent to one of ordinary skill in the art that modifications and variations to the invention may be made without departing from the spirit and scope of the invention. Therefore, the scope of the invention will be defined by the appended claims.

What is claimed is:

1. A biological detecting cartridge, adapted to gather a detected fluid, comprising:
   a collection port;
   a first flowing layer structure, communicating with the collection port; and
   a second flowing layer structure, communicating with the first flowing layer structure,
   wherein the first and the second flowing layer structures are disposed in different levels in the biological detecting cartridge,
   wherein the first flowing layer structure comprises:
   a first flowing channel, communicating with the collection port and comprising a plurality of first sections connected in series, wherein two adjacent first sections of the plurality first sections are connected with an angle; and
   a separation tank, connected to a connection of two adjacent first sections of the plurality first sections, and an extension direction of the separation tank is parallel to one of the connected first sections.

2. The biological detecting cartridge according to claim 1, wherein the first and the second flowing layer structures partially overlap with each other.

3. The biological detecting cartridge according to claim 1, wherein the second flowing layer structure comprises at least one branch structure, and the branch structure comprises:
   a quantification tank, communicating with the first flowing channel;
   a second flowing channel, communicating with the quantification tank and comprising a plurality of second sections connected in series, wherein two adjacent second sections of the plurality second sections are connected with an angle;
   a first mixing tank, communicating with the second flowing channel; and
   a second mixing tank, communicating with the second flowing channel and communicating with the first mixing tank.

4. A biological detecting cartridge, adapted to gather a detected fluid, comprising:
   a collection port;
   a first flowing layer structure, communicating with the collection port; and
   a second flowing layer structure, communicating with the first flowing layer structure,
   wherein the first and the second flowing layer structures are disposed in different levels in the biological detecting cartridge,
   wherein the first flowing layer structure comprises a first flowing channel, and the second flowing layer structure comprises at least one branch structure, wherein the first flowing channel has a narrowed channel and a communication hole corresponding to the branch structure, and the first flowing channel communicates with the branch structure through the communication hole,
   wherein a flow section width of the communication hole is greater than a flow section width of the narrowed channel, and the communication hole is located at a side of the narrowed channel where the detected fluid enters.

5. A biological detecting cartridge, adapted to gather a detected fluid, comprising:
   a collection port;
   a first flowing layer structure, communicating with the collection port; and
   a second flowing layer structure, communicating with the first flowing layer structure,
   wherein the first and the second flowing layer structures are disposed in different levels in the biological detecting cartridge,
   wherein the first flowing layer structure comprises a first flowing channel, and the second flowing layer structure comprises at least one branch structure, wherein the first flowing channel has a separator and a communication hole corresponding to the branch structure, and the first flowing channel communicates with the branch structure through the communication hole.

6. The biological detecting cartridge according to claim 5, wherein the separator is located on the communication hole to divide the communication hole into an inlet and an outlet, wherein the inlet and the outlet of the communication hole are respectively located at two sides of the separator.

7. A flowing method of a detected fluid in a biological detecting cartridge, wherein the biological detecting cartridge comprises: a collection port; a first flowing layer structure communicating with the collection port; and a second flowing layer structure communicating with the first flowing layer structure, the flowing method comprising:
   providing a detected fluid to a biological detecting cartridge;
   at a first time point, applying a first driving force corresponding to a first direction related to the biological detecting cartridge to the detected fluid in the biological detecting cartridge; and
   at a second time point, applying a second driving force corresponding to a second direction related to the biological detecting cartridge to the detected fluid in the biological detecting cartridge, wherein the first direction is different from the second direction,
   wherein the first flowing layer structure comprises a connection section, the second flowing layer structure comprises a quantification tank, and the connection section is connected with the quantification tank, wherein the flowing method of the detected fluid further comprises:
   at a third time point, applying a third driving force in parallel to an extension direction of the connection section to the detected fluid in the biological detecting cartridge, so as to drive the detected fluid to flow along the connection section,
   wherein when the detected fluid flows through the quantification tank, the detected fluid flows into and fills the quantification tank, and the overflowing detected fluid flows along the connection section.

8. The flowing method of the detected fluid in the biological detecting cartridge according to claim 7, wherein the connection section has a narrowed channel and a communication hole corresponding to the quantification tank, the connection section communicates with the quantification tank through the communication hole, and a flow section width of the communication hole is greater than a flow section width of the narrowed channel, wherein when the detected fluid flows through the quantification tank, the detected fluid flows through the communication hole into and fills the quantification tank, and the overflowing detected fluid flows through the narrowed channel and flows along the connection section.

9. The flowing method of the detected fluid in the biological detecting cartridge according to claim 7, wherein the connection section has a separator and a communication hole corresponding to the quantification tank, the connection section communicates with the quantification tank through the communication hole, the separator is located on the communication hole to divide the communication hole into an inlet and an outlet, and the inlet and the outlet of the communication hole are respectively located at two sides of the separator,
wherein when the detected fluid flows through the quantification tank, the detected fluid flows through the inlet of the communication hole into and fills the quantification tank, and the overflowing detected fluid flows back to the connection section through the outlet of the communication hole and flows along the connection section.

10. A flowing method of a detected fluid in a biological detecting cartridge, comprising:
providing a detected fluid to the biological detecting cartridge;
at a first time point, applying a first driving force corresponding to a first direction related to the biological detecting cartridge to the detected fluid in the biological detecting cartridge; and
at a second time point, applying a second driving force corresponding to a second direction related to the biological detecting cartridge to the detected fluid in the biological detecting cartridge, wherein the first direction is different from the second direction,
wherein the biological detecting cartridge comprises: a first mixing tank; and a second mixing tank communicating with the first mixing tank,
wherein the flowing method of the detected fluid further comprises:
at a third time point, applying a third driving force toward an extension direction of the first mixing tank to the detected fluid in the biological detecting cartridge, so as to drive the detected fluid to flow into the first mixing tank; and
at a fourth time point, applying a fourth driving force toward an extension direction of the second mixing tank to the detected fluid in the biological detecting cartridge, so as to drive the detected fluid to flow into the second mixing tank from the first mixing tank,
wherein the extension direction of the first mixing tank is different from the extension direction of the second mixing tank.

11. The flowing method of the detected fluid in the biological detecting cartridge according to claim 10, further comprising:
at a fifth time point, applying the third driving force toward the extension direction of the first mixing tank to the detected fluid in the biological detecting cartridge, so as to drive the detected fluid to flow into the first mixing tank from the second mixing tank.

* * * * *